Figure 4:
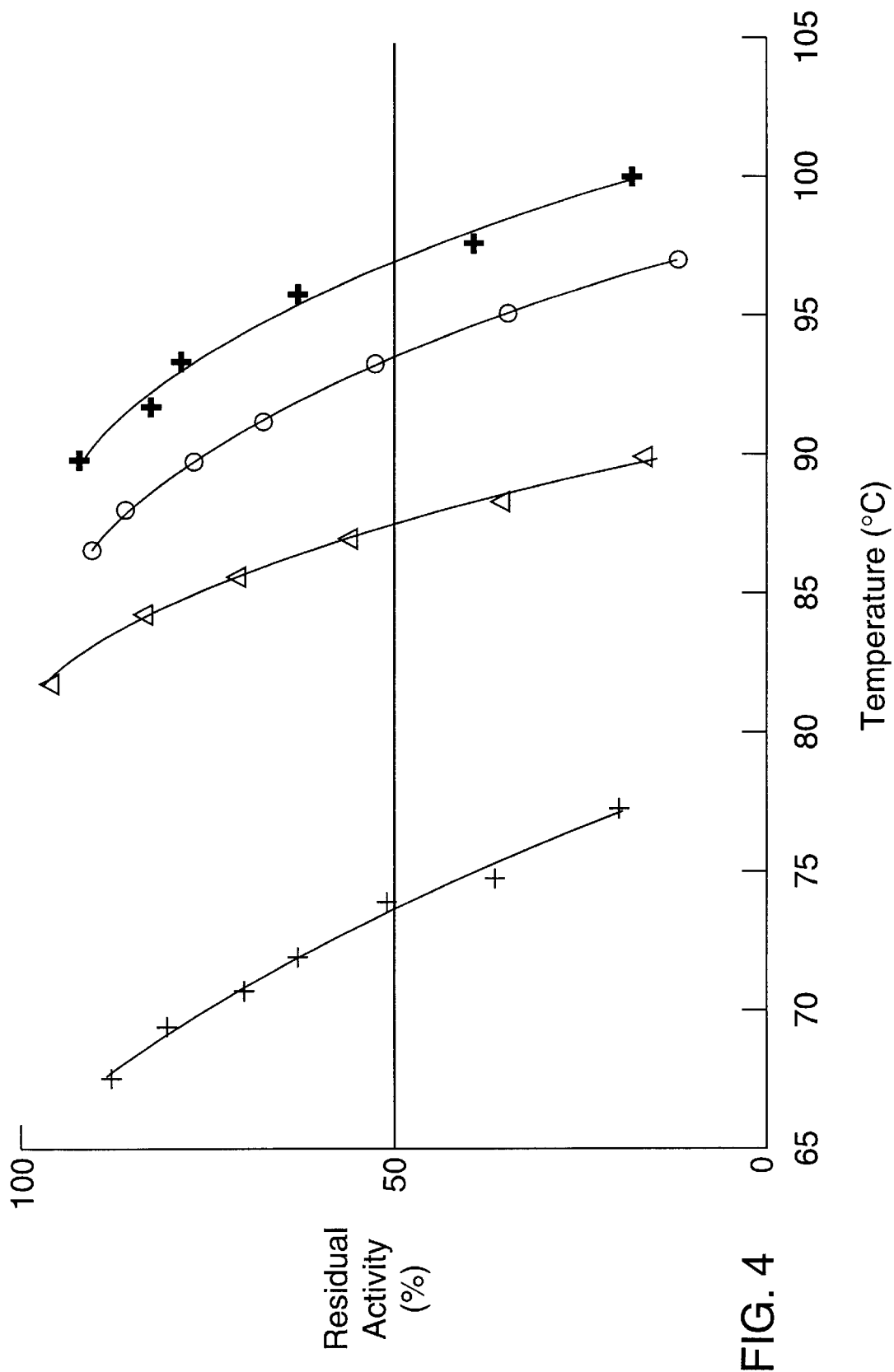

United States Patent [19]
Venema et al.

[11] Patent Number: 6,103,512
[45] Date of Patent: Aug. 15, 2000

[54] **THERMOSTABLE VARIANTS OF NEUTRAL PROTEASES OF *BACILLUS STEAROTHERMOPHILUS* AND *BACILLUS THERMOPROTEOLYTICUS***

[75] Inventors: Gerhardus Venema; Vincentius Eijsink, both of Groningen, Netherlands

[73] Assignee: Rijksuniversiteit Te Groningen, Netherlands

[21] Appl. No.: 08/682,643

[22] PCT Filed: Jan. 26, 1995

[86] PCT No.: PCT/NL95/00037

§ 371 Date: Sep. 19, 1996

§ 102(e) Date: Sep. 19, 1996

[87] PCT Pub. No.: WO95/20663

PCT Pub. Date: Aug. 3, 1995

[30] Foreign Application Priority Data

Jan. 27, 1994 [EP] European Pat. Off. .............. 94200182

[51] Int. Cl.[7] ................................. C12N 9/50; C12N 9/54
[52] U.S. Cl. .......................... 435/219; 435/221; 536/23.2
[58] Field of Search ..................................... 435/221, 212, 435/219, 220, 222, 68.1, 320.1, 252.3; 536/23.1, 23.2, 23.7

[56] References Cited

U.S. PATENT DOCUMENTS 5,340,735   8/1994   Christianson et al. ................... 435/221

OTHER PUBLICATIONS

Eijsink et al. "Structural determination of the thermostability of thermolysin–like Bacillus neutral proteases" in Stability and stabilization of enzymes, Proceedings of an International symposium held in Maastricht, The Netherland, Nov. 22–25, 1992, 1993.

van den Burg et al. "A highly thermostable neutral protease from *Bacillus caldolyticus* . . . " J. Bacteriol. 173, 4107–4115, Jul. 1991.

Hardy et al. "Stabilization of *Bacillus stearothermophilius* neutral protease by introduction of prolines" FEBS Lett. 317, 89–92, Feb. 1993.

Kubo et al. "Alteration of specific activity and stability of . . . " Appl. Envirn. Microbiol. 58, 3779–3783, Nov. 1992.

*Primary Examiner*—Nashaat T. Nashed
*Attorney, Agent, or Firm*—Michaelson & Wallace; Peter L. Michaelson

[57] ABSTRACT

The present invention provides genes encoding extremely thermostable variants of neutral proteases, as well as, vectors and cells comprising these genes and proteases produced through these genes, vectors and/or cells. In particular variants of the neutral proteases of *Bacillus stearothermophilus* and *Bacillus thermoproteolyticus* (thermolysine) and sequences and cells coding therefor are provided.

2 Claims, 6 Drawing Sheets

```
nprT:    GCAACCGATGGGGCCATTTTGAATAAGTTCAACCAAATCGACAGCCGCCAGCCCGGCGGC
                                                                         17
NP-ste:               ValAlaGlyAlaSerThrValGlyValGlyArgGlyValLeuGlyAspGln
nprT:    GGGCAGCCGGTCGCCGGCGCGTCGACGGTCGGCGTGGGCCGGGGTGTGTTGGGGGATCAG
                                                                         37
NP-ste:  LysTyrIleAsnThrThrTyrSerSerTyrTyrGlyTyrTyrTyrLeuGlnAspAsnThr
nprT:    AAATATATCAATACGACGTATTCCTCGTATTACGGCTACTACTATTTGCAAGACAATACG
                                                                         57
NP-ste:  ArgGlySerGlyIlePheThrTyrAspGlyArgAsnArgThrValLeuProGlySerLeu
nprT:    CGCGGCAGCGGCATTTTTACGTATGACGGACGAAACCGCACCGTTTTGCCCGGCAGCTTG
                                                                         77
NP-ste:  TrpThrAspGlyAspAsnGlnPheThrAlaSerTyrAspAlaAlaAlaValAspAlaHis
nprT:    TGGACCGATGGCGACAACCAATTTACCGCCAGCTATGACGCGGCGGCCGTGGACGCCCAT
                                                                         97
NP-ste:  TyrTyrAlaGlyValValTyrAspTyrTyrLysAsnValHisGlyArgLeuSerTyrAsp
nprT:    TATTACGCCGGCGTCGTGTATGATTACTACAAAAATGTGCACGGCCGGCTGAGCTATGAC
                                                                         117
NP-ste:  GlySerAsnAlaAlaIleArgSerThrValHisTyrGlyArgGlyTyrAsnAsnAlaPhe
nprT:    GGCAGCAACGCCGCCATCCGTTCGACCGTCCATTATGGCCGCGGCTACAACAACGCGTTT
                                                                         137
NP-ste:  TrpAsnGlySerGlnMetValTyrGlyAspGlyAspGlyGlnThrPheLeuProPheSer
nprT:    TGGAACGGTTCGCAAATGGTGTACGGCGATGGCGACGGACAGACGTTTTTGCCGTTTTCC
                                                                         157
NP-ste:  GlyGlyIleAspValValGlyHisGluLeuThrHisAlaValThrAspTyrThrAlaGly
nprT:    GGCGGCATTGACGTCGTGGGGCATGAGTTGACCCATGCGGTGACGGATTATACGGCCGGG
                                                                         177
NP-ste:  LeuValTyrGlnAsnGluSerGlyAlaIleAsnGluAlaMetSerAspIlePheGlyThr
nprT:    CTTGTTTACCAAAACGAATCTGGCGCCATCAATGAAGCGATGTCCGATATTTTCGGCACG
                                                                         197
NP-ste:  LeuValGluPheTyrAlaAsnArgAsnProAspTrpGluIleGlyGluAspIleTyrThr
nprT:    CTCGTGGAGTTCTACGCCAACCGCAACCCGGACTGGGAGATTGGCGAAGACATTTACACG
                                                                         217
NP-ste:  ProGlyValAlaGlyAspAlaLeuArgSerMetSerAspProAlaLysTyrGlyAspPro
nprT:    CCTGGGGTCGCCGGCGATGCGCTCCGCTCGATGTCCGACCCGGCAAATACGGCGATCCG
                                                                         237
NP-ste:  AspHisTyrSerLysArgTyrThrGlyThrGlnAspAsnGlyGlyValHisThrAsnSer
nprT:    GATCATTATTCCAAACGGTACACCGGCACGCAAGACAACGGCGGCGTCCATACAAACAGC
                                                                         257
NP-ste:  GlyIleIleAsnLysAlaAlaTyrLeuLeuSerGlnGlyGlyValHisTyrGlyValSer
nprT:    GGCATCATCAATAAAGCGGCGTACTTGCTCAGCCAAGGCGGCGTCCATTATGGCGTGAGC
                                                                         277
NP-ste:  ValThrGlyIleGlyArgAspLysMetGlyLysIlePheTyrArgAlaLeuValTyrTyr
nprT:    GTCAACGGCATCGGCCGCGACAAAATGGGGAAAATTTTCTACCGGGCGCTTGTCTACTAT
                                                                         297
NP-ste:  LeuThrProThrSerAsnPheSerGlnLeuArgAlaAlaCysValGlnAlaAlaAlaAsp
nprT:    TTGACGCCGACGTCGAACTTCAGCCAGCTGCGTGCCGCCTGCGTGCAAGCGGCCGCTGAT
                                                                         317
NP-ste:  LeuTyrGlySerThrSerGlnGluValAsnSerValLysGlnAlaPheAsnAlaValGly
nprT:    TTGTACGGGTCGACAAGCCAAGAAGTCAACTCGGTGAAACAGGCGTTCAATGCGGTTGGA
                    319
NP-ste:  ValTyrEnd
nprT:    GTGTATTAAGACGATGAGGTCGTACGCGT
```

FIG. 1

```
tln:                    GCCGTAGACGGAAAAATTTTAAATAAATTTAACCAACTTGACGCCGCAAAA
                                                                                    14
TLN:                              IleThrGlyThrSerThrValGlyValGlyArgGlyValLeu
tln:    CCAGGTGATGTGAAGTCGATAACAGGAACATCAACTGTCGGAGTGGGAAGAGGAGTACTT
                                                                                    34
TLN:    GlyAspGlnLysAsnIleAsnThrThrTyrSerSerTyrTyrTyrLeuGlnAspAsnThr
tln:    GGTGATCAAAAAAATATTAATACAACCTACTCTAGCTACTACTATTTACAAGATAATACG
                                                                                    54
TLN:    ArgGlyAsnGlyIlePheThrTyrAspAlaLysTyrArgThrThrLeuProGlySerLeu
tln:    CGTGGAAATGGGATTTTCACGTATGATGCGAAATACCGTACGACATTGCCGGGAAGCTTA
                            * * *
                                                                                    74
TLN:    TrpAlaAspAlaAspAsnGlnPhePheAlaSerTyrAspAlaProAlaValAspAlaHis
tln:    TGGGCAGATGCAGATAACCAATTTTTTGCGAGCTATGATGCTCCAGCGGTTGATGCTCAT
                                                                                    94
TLN:    TyrTyrAlaGlyValThrTyrAspTyrTyrLysAsnValHisAsnArgLeuSerTyrAsp
tln:    TATTACGCTGGTGTGACATATGACTACTATAAAAATGTTCATAACCGTCTCAGTTACGAC
                                                                                    114
TLN:    GlyAsnAsnAlaAlaIleArgSerSerValHisTyrSerGlnGlyTyrAsnAsnAlaPhe
tln:    GGAAATAATGCAGCTATTAGATCATCCGTTCATTATAGCCAAGGCTATAATAACGCATTT
                                                                                    134
TLN:    TrpAsnGlySerGlnMetValTyrGlyAspGlyAspGlyGlnThrPheIleProLeuSer
tln:    TGGAACGGTTCGCAAATGGTGTATGGCGATGGTGATGGTCAAACATTTATTCCACTTTCT
                            * * *
                                                                                    154
TLN:    GlyGlyIleAspValValAlaHisGluLeuThrHisAlaValThrAspTyrThrAlaGly
tln:    GGTGGTATTGATGTGGTCGCTCATGAGTTAACGCATGCCGTAACCGATTATACAGCCGGA
                                                                                    174
TLN:    LeuIleTyrGlnAsnGluSerGlyAlaIleAsnGluAlaIleSerAspIlePheGlyThr
tln:    CTCATTTATCAAAACGAATCTGGTGCAATTAATGAGGCAATATCTGATATTTTGGAACG
                                                                                    194
TLN:    LeuValGluPheTyrAlaAsnLysAsnProAspTrpGluIleGlyGluAspValTyrThr
tln :   TTAGTCGAATTTTACGCTAACAAAAATCCAGATTGGGAAATTGGAGAGGATGTGTATACA
                                                                                    214
TLN:    ProGlyIleSerGlyAspSerLeuArgSerMetSerAspProAlaLysTyrGlyAspPro
tln:    CCTGGTATTTCAGGGGATTCGCTCCGTTCGATGTCCGATCCGGCAAAGTATGGTGATCCA
                                                                                    217
                                                                                    234
TLN:    AspHisTyrSerLysArgTyrThrGlyThrGlnAspAsnAlaGlyValHisIleAsnSer
tln:    GATCACTATTCAAAGCGCTATACAGGCACGCAAGATAATGCCGGGGTTCATATCAATAGC
                                                                                    254
TLN:    GlyIleIleAsnLysAlaAlaTyrLeuIleSerGlnGlyGlyThrHisTyrGlyValSer
tln:    GGAATTATCAACAAAGCCGCTTATTTGATTAGCCAAGGCGGTACGCATTACGGTGTGAGT
                                                                                    274
TLN:    ValValGlyIleGlyArgAspLysLeuGlyLysIlePheTyrArgAlaLeuThrGlnTyr
tln:    GTTGTCGGAATCGGACGCGATAAATTGGGGAAAATTTTCTATCGTGCATTAACGCAATAT
                                                                                    294
TLN:    LeuThrProThrSerAsnPheSerGlnLeuArgAlaAlaAlaValGlnSerAlaThrAsp
tln:    TTAACACCAACGTCCAACTTTAGCCAACTTCGTGCTGCCGCTGTTCAATCAGCCACTGAC
                                                                                    314
TLN:    LeuTyrGlySerThrSerGlnGluValAlaSerValLysGlnAlaPheAspAlaValGly
tln:    TTGTACGGTTCGACAAGCCAGGAAGTCGCTTCTGTGAAGCAGGCCTTTGATGCGGTAGGG
                316
TLN:    ValLysEnd
tln:    GTGAAATAAAGTGGTATCTCATCAGTGGG
```

FIG. 2

```
tln:    GCCGTAGACGGAAAAATTTTAAATAAATTTAACCAACTTGACGCCGCAAAACCAGGTGAT
nprT:   GCAACCGATGGGGCCATTTTGAATAAGTTCAACAAATCGACAGCCGCCAGCCCGGCGGC
                                                                    17
tln:    GTGAAGTCGATAACAGGAACATCAACTGTCGGAGTGGGAAGAGGAGTACTTGGTGATCAA
TLN:            IleThrGlyThrSerThrValGlyValGlyArgGlyValLeuGlyAspGln
NP-ste:         ValAlaGlyAlaSerThrValGlyValGlyArgGlyValLeuGlyAspGln
nprT:   GGGCAGCCGGTCGCCGGCGCGTCGACGGTCGGCGTGGGCCGGGGTGTGTTGGGGGATCAG
                                                                    17
                                                                    34
tln:    AAAAATATTAATACAACCTACTCTACG            TACTACTATTTACAAGATAATACG
TLN:    LysAsnIleAsnThrThrTyrSerThr            TyrTyrTyrLeuGlnAspAsnThr
NP-ste: LysTyrIleAsnThrThrTyrSerSerTyrTyrGlyTyrTyrTyrLeuGlnAspAsnThr
nprT:   AAATATATCAATACGACGTATTCCTCGTATTACGGCTACTACTATTTGCAAGACAATACG
                                                                    37
                                                                    54
tln:    CGTGGAAATGGGATTTTCACGTATGATGCGAAATACCGTACGACATTGCCGGGAAGCTTA
TLN:    ArgGlyAsnGlyIlePheThrTyrAspAlaLysTyrArgThrThrLeuProGlySerLeu
NP-ste: ArgGlySerGlyIlePheThrTyrAspGlyArgAsnArgThrValLeuProGlySerLeu
nprT:   CGCGGCAGCGGCATTTTTACGTATGACGGACGAAACCGCACCGTTTTGCCCGGCAGCTTG
         * * *                                                      57
                                                                    74
tln:    TGGGCAGATGCAGATAACCAATTTTTTGCGAGCTATGATGCTCCAGCGGTTGATGCTCAT
TLN:    TrpAlaAspAlaAspAsnGlnPhePheAlaSerTyrAspAlaProAlaValAspAlaHis
NP-ste: TrpThrAspGlyAspAsnGlnPheThrAlaSerTyrAspAlaAlaAlaValAspAlaHis
nprT:   TGGACCGATGGCGACAACCAATTTACCGCCAGCTATGACGCGGCGGCCGTGGACGCCCAT
                                                                    77
                                                                    94
tln:    TATTACGCTGGTGTGACATATGACTACTATAAAAATGTTCATAACCGTCTCAGTTACGAC
TLN:    TyrTyrAlaGlyValThrTyrAspTyrTyrLysAsnValHisAsnArgLeuSerTyrAsp
NP-ste: TyrTyrAlaGlyValValTyrAspTyrTyrLysAsnValHisGlyArgLeuSerTyrAsp
nprT:   TATTACGCCGGCGTCGTGTATGATTACTACAAAAATGTGCACGGCCGGCTGAGCTATGAC
                                                                    97
                                                                    114
tln:    GGAAATAATGCAGCTATTAGATCATCCGTTCATTATAGCCAAGGCTATAATAACGCATTT
TLN:    GlyAsnAsnAlaAlaIleArgSerSerValHisTyrSerGlnGlyTyrAsnAsnAlaPhe
NP-ste: GlySerAsnAlaAlaIleArgSerThrValHisTyrGlyArgGlyTyrAsnAsnAlaPhe
nprT:   GGCAGCAACGCCGCCATCCGTTCGACCGTCCATTATGGCCGCGGCTACAACAACGCGTTT
                                                                    117
                                                                    134
tln:    TGGAACGGTTCGCAAATGGTGTATGGCGATGGTGATGGTCAAACATTTATTCCACTTTCT
TLN:    TrpAsnGlySerGlnMetValTyrGlyAspGlyAspGlyGlnThrPheIleProLeuSer
NP-ste: TrpAsnGlySerGlnMetValTyrGlyAspGlyAspGlyGlnThrPheLeuProPheSer
nprT:   TGGAACGGTTCGCAAATGGTGTACGGCGATGGCGACGGACAGACGTTTTTGCCGTTTTCC
         * * *                                                      137
                                                                    154
tln:    GGTGGTATTGATGTGGTCGCACATGAGTTAACGCATGCGGTAACCGATTATACAGCCGGA
TLN:    GlyGlyIleAspValValAlaHisGluLeuThrHisAlaValThrAspTyrThrAlaGly
NP-ste: GlyGlyIleAspValValGlyHisGluLeuThrHisAlaValThrAspTyrThrAlaGly
nprT:   GGCGGCATTGACGTCGTGGGGCATGAGTTGACCCATGCGGTGACGGATTATACGGCCGGG
                                                                    157
                                                                    174
tln:    CTCATTTATCAAAACGAATCTGGTGCAATTAATGAGGCAATATCTGATATTTTTGGAACG
TLN:    LeuIleTyrGlnAsnGluSerGlyAlaIleAsnGluAlaIleSerAspIlePheGlyThr
NP-ste: LeuValTyrGlnAsnGluSerGlyAlaIleAsnGluAlaMetSerAspIlePheGlyThr
nprT:   CTTGTTTACCAAAACGAATCTGGCGCCATCAATGAAGCGATGTCCGATATTTTCGGCACG
                                                                    177
```

FIG. 3A

```
                                                                                  194
tln:     TTAGTCGAATTTTACGCTAACAAAAATCCAGATTGGGAAATTGGAGAGGATGTGTATACA
TLN:     LeuValGluPheTyrAlaAsnLysAsnProAspTrpGluIleGlyGluAspValTyrThr
NP-ste:  LeuValGluPheTyrAlaAsnArgAsnProAspTrpGluIleGlyGluAspIleTyrThr
nprT:    CTCGTGGAGTTCTACGCCAACCGCAACCCGGACTGGGAGATTGGCGAAGACATTTACACG
                                                                                  197

214
tln:     CCTGGTATTTCAGGGGATTCGCTCCGTTCGATGTCCGATCCGGCAAAGTATGGTGATCCA
TLN:     ProGlyIleSerGlyAspSerLeuArgSerMetSerAspProAlaLysTyrGlyAspPro
NP-ste:  ProGlyValAlaGlyAspAlaLeuArgSerMetSerAspProAlaLysTyrGlyAspPro
nprT:    CCTGGGGTCGCCGGCGATGCGCTCCGCTCGATGTCCGACCCGGCGAAATACGGCGATCCG
                                                                                  217

234
tln:     GATCACTATTCAAAGCGCTATACAGGCACGCAAGATAATGGCGGGGTTCATATCAATAGC
TLN:     AspHisTyrSerLysArgTyrThrGlyThrGlnAspAsnGlyGlyValHisIleAsnSer
NP-ste:  AspHisTyrSerLysArgTyrThrGlyThrGlnAspAsnGlyGlyValHisThrAsnSer
nprT:    GATCATTATTCCAAACGGTACACCGGCACGCAAGACAACGGCGGCGTCCATACAAACAGC
                                                                                  237

254
tln:     GGAATTATCAACAAAGCCGCTTATTTGATTAGCCAAGGCGGTACGCATTACGGTGTGAGT
TLN:     GlyIleIleAsnLysAlaAlaTyrLeuIleSerGlnGlyGlyThrHisTyrGlyValSer
NP-ste:  GlyIleIleAsnLysAlaAlaTyrLeuLeuSerGlnGlyGlyValHisTyrGlyValSer
nprT:    GGCATCATCAATAAAGCGGCGTACTTGCTCAGCCAAGGCGGCGTCCATTATGGCGTGAGC
                                                                                  257

274
tln:     GTTGTCGGAATCGGACGCGATAAATTGGGGAAAATTTTCTATCGTGCATTAACGCAATAT
TLN:     ValValGlyIleGlyArgAspLysLeuGlyLysIlePheTyrArgAlaLeuThrGlnTyr
NP-ste:  ValThrGlyIleGlyArgAspLysMetGlyLysIlePheTyrArgAlaLeuValTyrTyr
nprT:    GTCAACGGCATCGGCCGCGACAAAATGGGGAAAATTTTCTACCGGGCGCTTGTCTACTAT
                                                                                  277

294
tln:     TTAACACCAACGTCCAACTTTAGCCAACTTCGTGCTGCCGCTGTTCAATCAGCCACTGAC
TLN:     LeuThrProThrSerAsnPheSerGlnLeuArgAlaAlaAlaValGlnSerAlaThrAsp
NP-ste:  LeuThrProThrSerAsnPheSerGlnLeuArgAlaAlaCysValGlnAlaAlaAlaAsp
nprT:    TTGACGCCGACGTCGAACTTCAGCCAGCTGCGTGCCGCCTGCGTGCAAGCGGCCGCTGAT
                                                                                  297

314
tln:     TTGTACGGTTCGACAAGCCAGGAAGTCGCTTCTGTGAAGCAGGCCTTTGATGCGGTAGGG
TLN:     LeuTyrGlySerThrSerGlnGluValAlaSerValLysGlnAlaPheAspAlaValGly
NP-ste:  LeuTyrGlySerThrSerGlnGluValAsnSerValLysGlnAlaPheAsnAlaValGly
nprT:    TTGTACGGGTCGACAAGCCAAGAAGTCAACTCGGTGAAACAGGCGTTCAATGCGGTTGGA
                                                                                  317

316
tln:     GTGAAATAAAGTGGTATCTCATCAGTGGG
TLN:     ValLysEnd
NP-ste:  ValTyrEnd
nprT:    GTGTATTAAGACGATGAGGTCGTACGCGT
          319
```

FIG. 3B

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 1049 base pairs
      (B) TYPE: nucleic acid (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 1:

```
GCAACCGATG GGGCCATTTT GAATAAGTTC AACCAAATCG ACAGCCGCCA GCCCGGCGGC      60

GGGCAGCCGG TCGCCGGCGC GTCGACGGTC GGCGTGGGCC GGGGTGTGTT GGGGGATCAG     120

AAATATATCA ATACGACGTA TTCCTCGTAT TACGGCTACT ACTATTTGCA AGACAATACG     180

CGCGGCAGCG GCATTTTTAC GTATGACGGA CGAAACCGCA CCGTTTTGCC CGGCAGCTTG     240

TGGACCGATG GCGACAACCA ATTTACCGCC AGCTATGACG CGGCGGCCGT GGACGCCCAT     300

TATTACGCCG GCGTCGTGTA TGATTACTAC AAAAATGTGC ACGGCCGGCT GAGCTATGAC     360

GGCAGCAACG CCGCCATCCG TTCGACCGTC CATTATGGCC GCGGCTACAA CAACGCGTTT     420

TGGAACGGTT CGCAAATGGT GTACGGCGAT GGCGACGGAC AGACGTTTTT GCCGTTTTTC     480

GGCGGCATTG ACGTCGTGGG GCATGAGTTG ACCCATGCGG TGACGGATTA TACGGCCGGG     540

CTTGTTTACC AAAACGAATC TGGCGCCATC AATGAAGCGA TGTCCGATAT TTTCGGCACG     600

CTCGTGGAGT TCTACGCCAA CCGCAACCCG GACTGGAGA TTGGCGAAGA CATTTACACG      660

CCTGGGGTCG CCGGCGATGC GCTCCGCTCG ATGTCCGACC CGGCGAAATA CGGCGATCCG     720

GATCATTATT CCAAACGGTA CACCGGCACG CAAGACAACG GCGGCGTCCA TACAAACAGC     780

GGCATCATCA ATAAAGCGGC GTACTTGCTC AGCCAAGGCG GCGTCCATTA TGGCGTGAGC     840

GTCAACGGCA TCGGCCGCGA CAAAATGGGG AAAATTTTCT ACCGGGCGCT TGTCTACTAT     900

TTGACGCCGA CGTCGAACTT CAGCCAGCTG CGTGCCGCCT GCGTGCAAGC GGCCGCTGAT     960

TTGTACGGGT CGACAAGCCA AGAAGTCAAC TCGGTGAAAC AGGCGTTCAA TGCGGTTGGA    1020

GTGTATTAAG ACGATGAGGT CGTACGCGT                                      1049
```

(2) INFORMATION FOR SEQ ID NO: 2:

(i) SEQUENCE CHARACTERISTICS:
        (A) LENGTH: 1040 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 2:

```
GCCGTAGACG GAAAAATTTT AAATAAATTT AACCAACTTG ACGCCGCAAA ACCAGGTGAT      60

GTGAAGTCGA TAACAGGAAC ATCAACTGTC GGAGTGGGAA GAGGAGTACT TGGTGATCAA     120

AAAAATATTA ATACAACCTA CTCTAGCTAC TACTATTTAC AAGATAATAC GCGTGGAAAT     180

GGGATTTTCA CGTATGATGC GAAATACCGT ACGACATTGC CGGGAAGCTT ATGGGCAGAT     240

GCAGATAACC AATTTTTTGC GAGCTATGAT GCTCCAGCGG TTGATGCTCA TTATTACGCT     300

GGTGTGACAT ATGACTACTA TAAAAATGTT CATAACCGTC TCAGTTACGA CGGAAATAAT     360

GCAGCTATTA GATCATCCGT TCATTATAGC CAAGGCTATA ATAACGCATT TTGGAACGGT     420

TCGCAAATGG TGTATGGCGA TGGTGATGGT CAAACATTTA TTCCACTTTC TGGTGGTATT     480
```

```
GATGTGGTCG CTCATGAGTT AACGCATGCC GTAACCGATT ATACAGCCGG ACTCATTTAT    540

CAAAACGAAT CTGGTGCAAT TAATGAGGCA ATATCTGATA TTTTTGGAAC GTTAGTCGAA    600

TTTTACGCTA ACAAAAATCC AGATTGGGAA ATTGGAGAGG ATGTGTATAC ACCTGGTATT    660

TCAGGGTATT CGCTCCGTTC GATGTCCGAT CCGGCAAAGT ATGGTGATCC AGATCACTAT    720

TCAAAGCGCT ATACAGGCAC GCAAGATAAT GCCGGGGTTC ATATCAATAG CGGAATTATC    780

AACAAAGCCG CTTATTTGAT TAGCCAAGGC GGTACGCATT ACGGTGTGAG TGTTGTCGGA    840

ATCGGACGCG ATAAATTGGG GAAAATTTTC TATCGTGCAT AACGCAATA TTTAACACCA     900

ACGTCCAACT TTAGCCAACT TCGTGCTGCC GCTGTTCAAT CAGCCACTGA CTTGTACGGT    960

TCGACAAGCC AGGAAGTCGC TTCTGTGAAG CAGGCCTTTG ATGCGGTAGG GGTGAAATAA   1020

AGTGGTATCT CATCAGTGGG                                               1040
```

(2) INFORMATION FOR SEQ ID NO: 3:

(i) SEQUENCE CHARACTERISTICS:
        (A) LENGTH: 319 amino acids
        (B) TYPE: amino acid
        (C) STRANDEDNESS: unknown
        (D) TOPOLOGY: unknown (ii) MOLECULE TYPE: protein (iii) HYPOTHETICAL: NO (iv) ANTI-SENSE: NO (xi) SEQUENCE DESCRIPTION: SEQ ID NO: 3:

```
Val Ala Gly Ala Ser Thr Val Gly Val Gly Arg Gly Val Leu Gly Asp
1               5                   10                  15

Gln Lys Tyr Ile Asn Thr Thr Tyr Ser Ser Tyr Tyr Gly Tyr Tyr Tyr
                20                  25                  30

Leu Gln Asp Asn Thr Arg Gly Ser Gly Ile Phe Thr Tyr Asp Gly Arg
                35                  40                  45

Asn Arg Thr Val Leu Pro Gly Ser Leu Trp Thr Asp Gly Asp Asn Gln
    50                  55                  60

Phe Thr Ala Ser Tyr Asp Ala Ala Val Asp Ala His Tyr Tyr Ala
65                  70                  75                  80

Gly Val Val Tyr Asp Tyr Tyr Lys Asn Val His Gly Arg Leu Ser Tyr
                85                  90                  95

Asp Gly Ser Asn Ala Ala Ile Arg Ser Thr Val His Tyr Gly Arg Gly
                100                 105                 110

Tyr Asn Asn Ala Phe Trp Asn Gly Ser Gln Met Val Tyr Gly Asp Gly
                115                 120                 125

Asp Gly Gln Thr Phe Leu Pro Phe Ser Gly Gly Ile Asp Val Val Gly
    130                 135                 140

His Glu Leu Thr His Ala Val Thr Asp Tyr Thr Ala Gly Leu Val Tyr
145                 150                 155                 160

Gln Asn Glu Ser Gly Ala Ile Asn Glu Ala Met Ser Asp Ile Phe Gly
                165                 170                 175

Thr Leu Val Glu Phe Tyr Ala Asn Arg Asn Pro Asp Trp Glu Ile Gly
                180                 185                 190

Glu Asp Ile Tyr Thr Pro Gly Val Ala Gly Asp Ala Leu Arg Ser Met
            195                 200                 205

Ser Asp Pro Ala Lys Tyr Gly Asp Pro Asp His Tyr Ser Lys Arg Tyr
    210                 215                 220
```

Thr Gly Thr Gln Asp Asn Gly Gly Val His Thr Asn Ser Gly Ile Ile
225                 230                 235                 240

Asn Lys Ala Ala Tyr Leu Leu Ser Gln Gly Gly Val His Tyr Gly Val
            245                 250                 255

Ser Val Thr Gly Ile Gly Arg Asp Lys Met Gly Lys Ile Phe Tyr Arg
            260                 265                 270

Ala Leu Val Tyr Tyr Leu Thr Pro Thr Ser Asn Phe Ser Gln Leu Arg
            275                 280                 285

Ala Ala Cys Val Gln Ala Ala Asp Leu Tyr Gly Ser Thr Ser Gln
    290                 295                 300

Glu Val Asn Ser Val Lys Gln Ala Phe Asn Ala Val Gly Val Tyr
305                 310                 315

(2) INFORMATION FOR SEQ ID NO: 4:

(i) SEQUENCE CHARACTERISTICS:
        (A) LENGTH: 316 amino acids
        (B) TYPE: amino acid
        (C) STRANDEDNESS: unknown
        (D) TOPOLOGY: unknown (ii) MOLECULE TYPE: protein (iii) HYPOTHETICAL: NO (iv) ANTI-SENSE: NO (xi) SEQUENCE DESCRIPTION: SEQ ID NO: 4:

Ile Thr Gly Thr Ser Thr Val Gly Val Gly Arg Gly Val Leu Gly Asp
1               5                   10                  15

Gln Lys Asn Ile Asn Thr Thr Tyr Ser Ser Tyr Tyr Leu Gln Asp
            20                  25                  30

Asn Thr Arg Gly Asn Gly Ile Phe Thr Tyr Asp Ala Lys Tyr Arg Thr
            35                  40                  45

Thr Leu Pro Gly Ser Leu Trp Ala Asp Ala Asp Asn Gln Phe Phe Ala
            50                  55                  60

Ser Tyr Asp Ala Pro Ala Val Asp Ala His Tyr Tyr Ala Gly Val Thr
65                  70                  75                  80

Tyr Asp Tyr Tyr Lys Asn Val His Asn Arg Leu Ser Tyr Asp Gly Asn
                85                  90                  95

Asn Ala Ala Ile Arg Ser Ser Val His Tyr Ser Gln Gly Tyr Asn Asn
            100                 105                 110

Ala Phe Trp Asn Gly Ser Gln Met Val Tyr Gly Asp Gly Asp Gly Gln
            115                 120                 125

Thr Phe Ile Pro Leu Ser Gly Gly Ile Asp Val Val Ala His Glu Leu
    130                 135                 140

Thr His Ala Val Thr Asp Tyr Thr Ala Gly Leu Ile Tyr Gln Asn Glu
145                 150                 155                 160

Ser Gly Ala Ile Asn Glu Ala Ile Ser Asp Ile Phe Gly Thr Leu Val
            165                 170                 175

Glu Phe Tyr Ala Asn Lys Asn Pro Asp Trp Glu Ile Gly Glu Asp Val
            180                 185                 190

Tyr Thr Pro Gly Ile Ser Gly Asp Ser Leu Arg Ser Met Ser Asp Pro
            195                 200                 205

Ala Lys Tyr Gly Asp Pro Asp His Tyr Ser Lys Arg Tyr Thr Gly Thr
            210                 215                 220

Gln Asp Asn Ala Gly Val His Ile Asn Ser Gly Ile Ile Asn Lys Ala

```
225                 230                 235                 240

Ala Tyr Leu Ile Ser Gln Gly Gly Thr His Tyr Gly Val Ser Val Val
                245                 250                 255

Gly Ile Gly Arg Asp Lys Leu Gly Lys Ile Phe Tyr Arg Ala Leu Thr
                260                 265                 270

Gln Tyr Leu Thr Pro Thr Ser Asn Phe Ser Gln Leu Arg Ala Ala Ala
            275                 280                 285

Val Gln Ser Ala Thr Asp Leu Tyr Gly Ser Thr Ser Gln Glu Val Ala
        290                 295                 300

Ser Val Lys Gln Ala Phe Asp Ala Val Gly Val Lys
305                 310                 315
```

THERMOSTABLE VARIANTS OF NEUTRAL PROTEASES OF *BACILLUS STEAROTHERMOPHILUS* AND *BACILLUS THERMOPROTEOLYTICUS*

This is a U.S. national stage application of PCT/NL95/00037 filed Jan. 26, 1995.

The present invention relates to metallo-endopeptidases, also called neutral proteases (NP's), that are produced, processed and secreted by members of the bacterial genus Bacillus. More specifically, it relates to the use of genetic manipulation techniques to alter genes encoding neutral proteases, such that the thermostability of the enzymes encoded by these genes is increased. The altered genes are also a part of the present invention, as are vectors and cells comprising said genes. The invention also relates to the production, processing and secretion of more stable neutral proteases derived from *B. stearothermophilus* by a *B. subtilis* strain carrying genes encoding these enzymes. More specifically, this invention relates to the introduction of a series of specific site-directed mutations in the gene encoding the neutral protease of *B. stearothermophilus*, which increase the thermostability of the product encoded by this gene. It also relates to a general analysis of the structural elements that determine the thermostability of the neutral protease of *B. stearothermophilus* and to the application of the results of this analysis for the stabilization of other neutral proteases, in particular thermolysin. The altered genes coding for the more stable thermolysin, as well as cells and vectors comprising such genes are also disclosed in the present invention. The invention also relates to the products of such genes, vectors and cells.

A general problem in the industrial use of enzymes is the stability of these catalysts. Enzymes are expensive and should preferably be usable in as low quantities and in as many process cycles as feasible. It is often desirable to conduct industrial processes at elevated temperatures (Nosoh and Sekiguchi, 1990; Kristjansson, 1989; Geisow, 1991). This limits the use of enzymes, since many enzymes do not sufficiently tolerate temperatures outside the physiological range. Thermostable enzymes are often more stable in general (Sonnleitner and Fiechter, 1983; Nosoh and Sekiguchi, 1990): they are more stable at any temperature and they have a higher resistance towards other denaturing factors such as extreme pH values, detergents and high salt concentrations. The availability of thermostable enzymes is therefore clearly desirable for the following reasons:

The temperature range at which enzymatically catalyzed processes can be conducted is expanded.

The enzymes last longer thus reducing the quantities needed.

NP's are used in several industrial processes, the most important of which is the preparation of the artificial sweetener aspartame (Gerhartz, 1990; Isowa et al., 1979). NP's are also employed in the leather and baking industry, in breweries, and in the production of protein hydrolysates in the leather industry and in breweries (Gerhartz, 1990). At present, mostly thermolysin (e.g. in the preparation of aspartame) and the neutral protease of *Bacillus subtilis* (e.g. for beer-brewing applications) are used in industrial processes. The costs of these processes could be reduced if more stable NP variants would be available. A recent paper by Kubo et al. (1992) is an illustration of the interest of the aspartame industry in this matter.

Several Bacilli are known to produce extra-cellular metallo-endopeptidases, also called neutral proteases. These enzymes contain 300–319 residues and are active in the neutral pH range. The best known NP is thermolysin, the highly thermostable 316 residue NP from *Bacillus thermoproteolyticus*. Bacilli exhibit considerable differences in growth temperature and the thermostabilities of their neutral proteases differ accordingly. Several Bacillus neutral proteases have been characterized and genes encoding for these enzymes have been cloned and sequenced from e.g. *B. subtilis* (Yang et al., 1984), *B. stearothermophilus* CU-21 (Fujii et al., 1983; Takagi et al., 1985), *B. stearothermophilus* MK-232 (Kubo & Imanaka, 1988), *B. thermoproteolyticus rokko* (Marquardt et al., 1990) and *B. caldolyticus* (Van den Burg et al., 1991). Using genetical techniques (such as 'site-directed mutagenesis', e.g. Stanssens et al., 1989) genes encoding neutral proteases have been mutated to change properties of the enzymes, such as thermostability (Imanaka et al., 1986; Toma et al., 1991; Van den Burg, 1991; Eijsink, 1991).

A piece of chromosomal *B. stearothermophilus* DNA containing the neutral protease gene (npr) has been cloned by Fujii et al. (1983) into plasmid pTB90; the resulting plasmid was designated pNP22. The npr gene was subcloned from pNP22 into pTZ12 (Aoki et al., 1987), resulting in pGE501 (Eijsink et al., 1990, 1992b). Plasmid pGE501 could be transformed to *Bacillus subtilis* strain DB 117 (Eijsink et al., 1990). *Bacillus subtilis* DB117 cells containing pGE501 (or a derivative thereof; see below) expressed, processed and secreted the neutral protease *B. stearothermophilus* (NP-ste). From plasmid pGE501 fragments containing parts of the neutral protease gene have been subcloned into *E. coli* plasmids pMa and pMc for site-directed mutagenesis according to Stanssens et al. (1989) (Eijsink et al., 1990). After site-directed mutagenesis npr genes containing the mutated fragment were reconstructed, yielding variants of pGE501. These variants of pGE501 were essentially identical to the original pGE501 plasmid, with the exception of one or more nucleotide changes in the npr gene that gave rise to one or more amino acid changes in the mature gene product. This genetic strategy has been used extensively by the inventors and several site-directed mutations in the npr gene that result in increased thermostability of the gene product have been described (Eijsink, 1991; Eijsink et al., 1991a; Van den Burg et al., 1991; Vriend et al., 1991; Eijsink et al., 1992a,b; Hardy et al., 1993; Eijsink et al., 1993).

The present invention povides strategies for the construction of extremely thermostable neutral proteases, which are far more stable than any naturally occurring or engineered neutral protease described so far.

It also provides the products resulting from said strategies as well as the use of said products in industrial processes and intermediates in making the products.

In the description of the present invention the thermostability of a neutral protease is defined by the 'T50' of the enzyme. The T50 is determined as follows: The *B. stearothermophilus* neutral protease is produced by a *B. subtilis* strain harbouring pGE501 or a mutated variant thereof and purified from the culture medium according to previously described methods (Van den Burg et al., 1989; Eijsink et al., 1991b). The purified enzyme is diluted to ±0.1 $\mu$M in 20 mM NaAc, pH 5.3, 5 mM $CaCl_2$, 0.5% isopropanol and 62.5 mM NaCl (final concentrations), and incubated for 30 minutes at various temperatures, ranging from 58 to 98° C. After incubation the residual proteolytic activity is determined and expressed as percentage of the initial activity. T50 is the temperature at which 50% of the initial activity is retained after the 30 minutes incubation period. In every thermostability assay a reference sample containing the wild-type *B.* stearothermophilus neutral protease is included and the thermostability of mutant neutral proteases is expressed as dT50, being the difference in T50 between the mutant and the wild-type enzyme. Temperatures were registered using mercury thermometers. Since in earlier publications results obtained using alcohol thermometers were given, and since the pH in the present thermostability assay was slightly higher than in earlier assays, the present data deviate slightly from earlier published data. Deviations in dT50 values are small. Deviations in T50 values are considerable (caused by the use of mercury instead of alcohol thermometers) and amount upto plus 6° C. in the >90° C. temperature range.

On the basis of previous results on NP thermostability it has been speculated that, at least under the conditions of the thermostability assay used in the present invention, the thermostability of an NP, and thus its T50, is determined by the rate at which local unfolding processes, that render the NP molecule susceptible to autolysis, occur (Eijsink et al., 1991c, 1992c; Vriend and Eijsink, 1993; see also Dahlquist et al., 1976 and Braxton and Wells, 1992). This presumed mechanism has several consequences (Vriend and Eijsink, 1993):

Mutations with large effects on thermostability of NPs should be mainly located at the surface of the protein. This was indeed observed in NP-ste (Eijsink et al., 1992b; Vriend and Eijsink, 1993).

Mutations with large positive or negative effects on NP thermostability should be located in regions that unfold relatively easily upon heating. Mutations aimed at stabilizing NPs are most effective if they are introduced in a region that unfolds relatively easily (in the remainder of the description such a region is called a 'weak region'). For NP-ste this consequence was partly sustained by experimental evidence: many mutations, in several parts of the protein had only marginal effects on thermostability, whereas mutations in the 66–72 region had large effects on thermostability. This suggests that the 66–72 region is part of a weak region in the enzyme (Vriend and Eijsink, 1993).

The identification of weak regions is essential for the successful design of a mutation strategy to stabilize NPs. In addition it is essential to know the relative importance and the total number of weak regions, as explained by Eijsink et al. (1992c).

The effects of mutations that stabilize the same local region of the NP (or, in other words, that affect the same pathway of local unfolding) are not additive. It is no use to 'over-stabilize' a weak region, because, after sufficient stabilization, unfolding in this region will no longer play a role in the overall process of thermal inactivation. This was indeed observed (Eijsink et al., 1992c). As long as the addition of extra stabilizing mutations to a region of the protein results in increased thermostability, this region must be considered as relatively weak. It means that any following stabilizing mutation in that region will increase the thermostability of the enzyme. Thus that region should be considered during the design of further stabilizing mutations. This is described in the present invention. In general, it is not to be expected that many mutations in the same region of the protein exhibit considerable additivity. This is only possible in case an NP has one weak region which is considerably weaker than any other unfolding region. Such a case is described in the present invention.

Information derived from a comparison of naturally occurring thermostable and thermolabile neutral proteases could help in the design of stabilization strategies for NPs. However, despite the availability of the primary structures of many NPs and the tertiary structures of an extremely thermostable (thermolysin; Holmes and Matthews, 1982) and a less thermostable (from *Bacillus cereus*; Stark et al., 1992) NP, the structural factors underlying the differences in thermostability between naturally occurring neutral proteases are largely unknown (see e.g. Stark et al., 1992). Site-directed mutagenesis studies have provided some insight in the structural differences that underly the difference in thermostability between thermolysin (T50=86.9° C.) and the less stable NP-ste (T50=73.4° C.; NP-ste and thermolysin have 85% sequence identity). This is shown in Table I.

Table I. Previously published analyses of the contribution of sequence differences between NP-ste and thermolysin to the difference in thermostability between these two enzymes. Residues in NP-ste (T50=73.4° C.) were replaced by the corresponding residue in thermolysin (T50=86.9° C.).

| Mutation: | dT50 (° C.) [1]: | Reference: |
| --- | --- | --- |
| Ala4 -> Thr | +1.9 | Van den Burg et al., 1991 |
| Gly47-Arg48-Asn49 -> Ala-Lys-Tyr | -0.2 | Eijsink et al., 1993 |
| Thr59 -> Ala | +1.9 | Van den Burg et al., 1991 |
| Gly61 -> Ala | [2] | Imanaka et al., 1986 |
| Thr66 -> Phe | +7.0 | Van den Burg et al., 1991 |
| Ala72 -> Pro | +6.3 | Hardy et al., 1993 |
| Gly92 -> Asn | -0.3 | Eijsink et al., 1993 |
| Gly144 -> Ala | +0.6 | Imanaka et al., 1986; Eijsink et al., 1993 |
| Arg185 -> Lys | -2.7 | Eijsink et al., 1993 |
| Ala204 -> Ser | -0.4 | Eijsink et al., 1993 |
| Cys291 -> Ala | 0 | Eijsink et al., 1992b, 1993 |
| Asn314 -> Asp | -0.3 | Eijsink et al., 1993 |

[1] Some dT50 values differ slightly from earlier published values, for reasons described above.
[2] This mutation was mentioned in a publication by Imanaka et al. (1986). In that publication stability data for this mutant are not given. The $T_{50}$ value for this mutation has not been published.

Since NP-ste and thermolysin have 85 percent sequence identity, these enzymes are expected to be highly similiar with respect to overall structure. Statistical analyses of similarities between the structures of homologous proteins have provided compelling evidence supporting this assumption (Chothia and Lesk, 1986; Sander and Schneider, 1991; Vriend and Eijsink, 1993). The high similarity between the two enzymes makes it plausible that the rate of their thermal inactivation is determined by unfolding of the same regions. The relative contribution of unfolding of the different weak regions to the overall thermal inactivation rate must differ between the two enzymes, since they have different thermostabilities. Because of the high similarity between the two enzymes it is also plausible that the introduction of mutations in thermolysin, that are reciprocal to the ones listed in Table 1, have effects on the thermostability of thermolysin that are reciprocal to the effects listed in Table I (at least qualitatively).

From the data in Table I and from results described by Eijsink et al. (1992b) it was concluded that the 66–72 region of NP-ste might be a region that unfolds relatively easily. In accordance with this conclusion and its assumed consequences (see above), it appeared that mutations at two other positions in this region (65 and 66) had relatively large effects on thermostability (Hardy et al., 1993). Replacing Ser65 by Pro increased the T50 of NP-ste by 4.7° C. (Hardy et al., 1993). The latter mutation was a so-called 'designed' mutation. In the present invention mutations are called 'designed' in case they have not been suggested by nature (through comparisons of homologous NP variants); instead, they have been 'designed' on the basis of the principles that (are generally supposed to) govern protein structure and stability.

On the basis of the results and theory described above, the aim of stabilizing NP-ste seems to be attainable by the following steps:

Combine the stabilizing mutations listed in Table I.

Analyze the importance of other structural differences between NP-ste and thermolysin. As a result of this analysis, essential knowledge concerning the structural factors that determine NP thermostability may be obtained. This knowledge is needed for the design of further stabilizing mutations. In addition, this analysis may result in the identification of 'new' mutations in NP-ste, that have a stabilizing effect. Thirdly, this analysis may help in identifying weak regions in the NPs.

Design and insert stabilizing mutations that stabilize against local unfolding in the 66–72 weak region of NP-ste.

Identify other weak regions (that is regions in which mutations have relatively large effects on thermostability) and introduce stabilizing mutations in those regions.

Combine all identified stabilizing mutations in all identified weak regions. Per weak region, the addition of stabilizing mutations should be continued till no further additivity is observed.

The novel strategy provided in the present invention gives a vast array of possibilities for obtaining additional mutated neutral proteases with enhanced thermostability.

In addition the invention provides unexpectedly stable proteases, which are more stable than thermolysin itself. Surprisingly, by providing more than one mutation in a weak region, optionally in combination with mutations in other weak regions, the thermostability still increased.

Moreover, it was unexpected that combinations of mutations designed on the basis of thermolysin would lead to more thermostable proteases than thermolysin itself.

From the foregoing it may be clear for what purpose the novel mutated proteases according to the invention can be used. Additional applications such as preparation of protein hydrolysates, etc. are readily available for the person skilled in the art.

The person skilled in the art will also realize that it is possible to use active fragments or derivatives of the proteases disclosed in the present invention. These fragments need only to be active and thermostable. Derivatives can be produced by changing amino acid residues in regions where they do not influence activity and/or thermostability.

The present invention provides essential information that enables even further stabilization of NP-ste through site-directed mutations. The present invention also shows clearly how thermolysin could be stabilized through site-directed mutations. Apart form the mutations in NP-ste and thermolysin that are obvious from the present invention, one could think of:

Rigidification of the N-terminal domain, especially of the 59–72 region and the N-terminal beta-hairpin (residues 1–25), by introduction of proline residues or by the introduction of disulfide bonds.

Mutations in the weak regions of NP-ste and thermolysin (as described and/or identified in the present invention), that are designed on the basis of general principles regarding protein structure and stability.

Identification of the auto-digestion sites that play a rate-limiting role in the process of thermal inactivation. Alteration of these autodigestion sites by site-directed mutations.

In relation to the use of enzymes in industry, often attempts to improve and change the specificity and activity of enzymes are made, using site-directed mutagenesis techniques. The enzymes in the present invention are a good starting point for such attempts. Successful manipulation of activity and specificity of the extremely stable enzymes presented here, would result in enzymes that are even more valuable for industry.

The extremely stable enzymes presented here are expected to be stable under several harsh conditions, since thermostable enzymes are often also relatively stable under for example extremes of pH or high salt concentrations (Sonnleitner and Fiechter, 1983). This increases the potential use of these enzymes in industry.

For reference, the experimental results related to the present invention can be compared to the results obtained by Imanaka et al. (1986), who described two stabilizing site-directed mutations in the neutral protease of *B. stearothermophilus*. They used an assay for thermostability that differs from the one used in the description of the present invention. The stabilizing replacement of Gly144 by Ala described by Imanaka et al. resulted in a dT50 of +0.6° C. in the thermostability assay used in relation to the present invention. The destabilizing replacement of Thr66 by Ser described by Imanaka et al. resulted in a dT50 of −4.4° C. in the thermostability assay used in relation to the present invention.

Methods

Plasmids and Strains

The *B. stearothermophilus* npr gene (taken from plasmid pNP22; Takagi et al., 1985; Fujii et al., 1983) was subcloned in the high copy number *B. subtilis* vector pTZ12 (Aoki et al., 1987, yieding pGE501 (Eijsink et al., 1990, 1992b). The gene was expressed in the protease deficient *B. subtilis* strain DB117 (Eijsink et al., 1990). Suitable fragments of the npr genes were subcloned in the *E. coli* plasmid pMa/c for site-directed mutagenesis (Stanssens et al., 1989). *E. coli* WK6 and WK6MutS (Zell and Fritz, 1987) were used in site-directed mutagenesis procedures. All strains were grown on Trypton-Yeast medium, containing appropriate antibiotics.

Site-directed Mutagenesis

The design of the mutagenic oligonucleotides used for the production of site specific mutations was such that a restriction site was removed or created to facilitate the selection of mutants, without producing additional changes at the amino acid level (Eijsink et al., 1990; Eijsink et al., 1992 c). Mutagenesis was performed using a gapped duplex method described earlier (Stanssens et al., 1989). Mutant clones were selected by restriction analysis and their npr gene fragment was sequenced using the dideoxy chain termination method (Sanger et al., 1977). For the production of mutant neutral proteases in *B. subtilis*, correctly mutated npr gene fragments were used to construct derivatives of pGE501 containing an intact mutant npr gene. Multiple mutations were constructed either by performing several subsequent mutagenesis steps (each step followed by sequence analysis of the mutated gene fragment), or by combining fragments of mutant genes using standard genetic techniques (Sambrook et al., 1989).

Production, Purification and Characterization of Neutral Proteases

*B. subtilis* DB117 harbouring a pGE501 variant was cultured in 600 ml medium in aerated 1000 ml flasks at 32°

C. After 16 hours of cultivation the cells were removed by centrifugation and the supernatants were loaded onto Bacitracin-silica columns (Unilever Research Laboratories, Vlaardingen, The Netherlands) for affinity chromatography as described before (Van den Burg et al., 1989). After purification the enzymes were stored at −18° C. in the elution buffer used in the affinity chromatography procedure (20 mM sodium acetate, pH 5.3; 5 mM $CaCl_2$, 20% (v/v) isopropanol; 2.5 M NaCl; 0.03% sodium azide). Purified enzyme was analysed using sodium dodecyl sulfate polyacrylamide gel electrophoresis (SDS-PAGE) as described before (Van den Burg et al., 1989).

For the determination of T50, aliquots of diluted pure enzyme (approximately 0.1 μM in 20 mM sodium acetate, pH 5.3, 5 mM $CaCl_2$, 0.5% (v/v) isopropanol, 62.5 mM NaCl) were incubated at appropriate temperatures. Subsequently, the residual protease activity was determined using a caseine assay (Fujii et al., 1983). The T50 and dT50 values presented in this invention are average values derived from at least three independent measurements. The standard deviation in T50 values is approximately 0.7° C.; the standard deviation in dT50 values is approximately 0.4° C.

The thermostability of NPs in time was determined under the same conditions as those used in the T50 determination. The enzyme was diluted and divided into aliquots. Some of the aliquots were stored on ice, whereas the others were incubated at 90° C. Aliquots were removed from the 90° C. incubator after different time intervals and subsequently stored on ice. At the end of the incubation period the (remaining) proteolytic activity in all aliquots was determined using the casein assay.

The reference thermolysin sample was purchased from Boehringer Mannheim. Before usage the enzyme was purified in a way identical to that employed for NP-ste.

Protein concentrations were determined using the MicroBCA assay supplied by Pierce.

Design and Structural Analysis of Mutations

The design of stabilizing mutations, theoretical analysis of the structural effects of mutations, and structural inspections of NP molecules were performed using in computo procedures that have extensively been described elsewhere (Eijsink et al., 1990; Vriend and Eijsink, 1993). The design of stabilizing mutations and all theoretical considerations were based on generally accepted principles of protein structure and stability as described by for example Matthews (1991), Alber (1991), Vriend and Eijsink (1993), Fersht and Serrano (1993).

Alternative Methods

In the present invention mutations were introduced by gapped-duplex site-directed mutagenesis into the gene encoding NP-ste. There are several alternative methods to obtain the variants of the NP-ste gene that are equivalent to the ones described in the present invention:

The use of other techniques for site-directed mutagenesis, such as PCR based methods.

The exchange of (part of) the natural gene by a synthetic gene that contains the correct mutations.

Mutagenesis of genes encoding other NPs (for example thermolysin), such as to obtain genes that are identical to the ones described in the present invention. There are also several methods to obtain genes that are not identical to the ones described in the present invention, but that encode neutral proteases that, with respect to structure and thermostability, essentially identical to the gene products described in the present invention:

Construct NP-ste variants that contain the stabilizing mutations described in the present invention plus one or more mutations that do not dramatically affect thermostability.

Construct variants of thermolysin in which residues have been replaced by the corresponding residue in NP-ste, for example Asn19→Tyr, Ser103 (106)→Thr en Lys182 (185) →Arg. In addition Ser68 may be replaced by Asp or Pro.

Construct chimeric (maybe partly synthetic) genes encoding NPs that contain the N-terminal part of thermolysin (Kubo et al., 1988; Marquardt et al., 1990) and the C-terminal part of wild-type NP-ste. The border between the thermolysin part and the NP-ste part could for example lie between residues 70 and 100.

The use of partly or completely synthetic genes encoding neutral proteases that, with respect to thermostability, are essentially identical to the ones described above.

A more general alternative method that is based on the present invention and that would result in genes encoding neutral proteases that, with respect to thermostability, are essentially identical to the ones described above is the following:

Introduce stabilizing mutations in the weak regions that have been identified in the present invention. NP-ste and thermolysin are likely to have the same weak regions, so this strategy could be conducted using either thermolysin or NP-ste as a starting point.

Alignment of Neutral Protease Amino Acid Sequences

NP-ste contains 319 residues (Takagi et al., 1985), see FIG. 1 and thermolysin contains 316 residues (Titani et al., 1972; Marquardt et al., 1990), see FIG. 2. In the present invention, the sequences of these two enzymes are aligned as depicted in FIG. 3. Residues 'correspond' if they are at the same position in the alignment depicted in FIG. 3. As a consequence of the extra three residues in NP-ste in the 25–30 region, the numbering of residues differs slightly between NP-ste and thermolysin. Some examples: Ala 4 in NP-ste (abbreviated to A in FIG. 3) corresponds with Thr 4 in thermolysin (abbreviated to T in FIG. 3); Arg 185 in NP-ste (abbreviated to R in FIG. 3) corresponds to Lys 182 (abbreviated to K in FIG. 3) in thermolysin.

Analysis of Differences Between NP-ste and Thermolysin

The gene encoding NP-ste was manipulated such as to change residues in the mature gene product by residues that occur at the corresponding position in thermolysin. The thermostabilities of the various mutants are listed in Table II.

Table II. Analyses of the contribution of sequence differences between NP-ste and thermolysin to the difference in thermostability between these two enzymes. Residues in NP-ste were replaced by the corresponding residue in thermolysin.

| Mutation | dT50 (° C.) |
| --- | --- |
| Tyr19 -> Asn | −2.7 |
| Gly61 -> Ala | +3.9 |
| Thr103 -> Ser | −5.9 |

Designed Stabilizing Mutations in NP-ste

The gene encoding NP-ste was manipulated such as to change Ser68 in the mature gene product by Asp. This resulted in an increase of T50 by 3.2° C. This mutation was designed on the basis of general principles governing protein structure and stability.

Construction of Extremely Stable Variants of NP-ste

Figure 5:
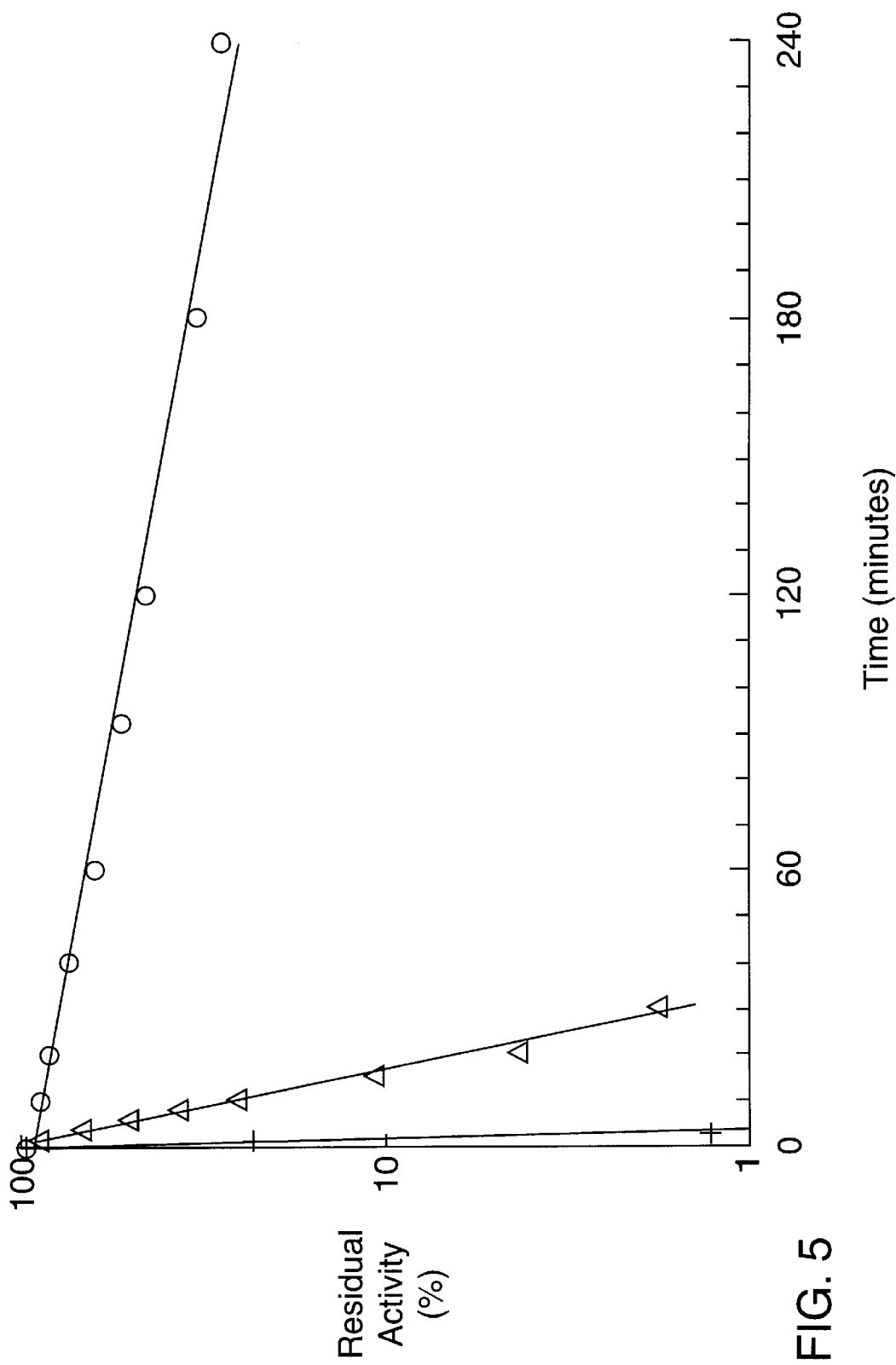

The gene encoding NP-ste was manipulated such as to change several residues in the mature gene product (as compared to the NP-ste wild-type enzyme). This resulted in changes in T50, as listed in Table III and depicted in FIGS. 4 and 5. Table III. Manipulation of the gene encoding NP-ste, such as to change several residues in the mature gene product; T50 of the mutant enzymes and the effect of the mutations (dT50, as compared to wild-type NP-ste) are given. For reference, the thermostabilities of thermolysin and NP-ste are also indicated. The mutations are indicated by number only; they concern Ala4→Thr (4), Thr59→Ala (59), Gly61→Ala (61), Thr66→Phe (66), Ser68→Asp (68-I), Ser68→Pro (68-II), Ala72→Pro (72)

| Mutations | dT50 (° C.) | T50 (° C.) |
|---|---|---|
| NP-ste | 0 | 73.4 |
| thermolysin | +13.5 | 86.9 |
| 66 + 72 | +12.3 | 85.7 |
| 59 + 66 + 72 | +14.4 | 87.8 |
| 61 + 66 + 72 | +15.7 | 89.1 |
| 59 + 61 + 66 + 72 | +18.8 | 92.2 |
| 4 + 59 + 66 + 72 | +15.7 | 89.1 |
| 4 + 61 + 66 + 72 | +17.2 | 90.6 |
| 4 + 59 + 61 + 66 + 72 | +19.9 | 93.3 |
| 59 + 61 + 66 + 68-I + 72 | +21.0 | 94.4 |
| 59 + 61 + 66 + 68-II + 72 | +21.7 | 95.1 |
| 4 + 59 + 61 + 66 + 68-I + 72 | +22.9 | 96.3 |
| 4 + 59 + 61 + 66 + 68-II + 72 | +23.5 | 96.9 |

General Characterization of the Mutant Enzymes

All mutant enzymes were characterized (in purified form) by SDS-PAGE and by determination of their specific activity towards casein. Using these analyses, all mutant enzymes described in the present invention were similar to the wild-type NP-ste enzyme with respect to these characteristics.

Identification and Characterization of Weak Regions in NP-ste

Large effects on thermostability indicate weak regions in the protein. The present results show that weak regions in NP-ste are located in the 59–72 region, and around residues 4, 19, 106, and 185. The effects of the mutations in the different regions indicate the relative contribution of each of the regions to the overall process of thermal inactivation.

NP-ste has a clearly weak region that can broadly be defined as the N-terminal half of the protein, or, more narrowly, as the region 59 till 72. Unfolding in this region must be highly predominant during heating of the protein, since mutations in the 59–72 result in extreme stabilization of the enzyme. Apparently, the region is not maximally stabilized in the invented mutants, since, in general, additivity of mutational effects is observed. Even the 'last' additional mutations still increased thermostability (see Table III): Adding Ser68→Asp or Ser68→Pro to the 4-59-61-66-72 five-fold mutant gave increases in T50 of 3.0° C. and 3.6° C., respectively. This indicates that further stabilizations could be achieved by additional mutations in the 59–72 region.

The residues 4, 19 and 106 are located relatively close to the 59–72 stretch, whereas residue 185 is located relatively far away. It is not clear whether residues 4, 19 and 106 should be considered to be part of the same weak region as the 59–72 stretch. In other words, it is not clear whether mutations at positions 4, 19 and 106 affect the same local unfolding pathway as mutations in the 59–72 stretch. Adding Ala4→Thr to the 59-61-66-68(I)-72 five-fold mutant or the 59-61-66-68(II)-72 five-fold mutant gives increases in T50 of 1.9° C. and 1.8° C., respectively. There are two possible explanations:

1. Residue 4 plays a role in a different local unfolding pathway.
2. Mutations at position 4 affect the same local unfolding pathway as mutations in the 59–72 stretch. Since this stretch is not yet maximally stabilized (see above), additivity of mutational effects is observed.

Regardless of the precise character of the local unfolding pathways in NP-ste, the present results and the theoretical considerations described above clearly indicate that stabilizing mutations at positions 4, 19, 106 and 185 and in their environment might be useful for further stabilization of the protease.

Thermolysin and NP-ste are highly similar enzymes and therefore the conclusions concerning weak regions and stabilization strategies drawn on the basis of experiments with NP-ste also apply to a certain extent to thermolysin. The replacement of only three residues in the N-terminal domain of NP-ste by the corresponding residue in thermolysin (combinations 59-66-72 and 61-66-72) was sufficient to make NP-ste more thermostable than thermolysin. Also, by replacing four or five residues in the N-terminal domain of NP-ste by the corresponding residue in thermolysin, NP-ste variants were obtained that are extremely stable and considerably more thermostable than thermolysin. From these observations, the following conclusions with respect to thermolysin can be drawn:

Thermolysin is not optimized for thermostability.

The N-terminal domain, especially the 56–69 (59–72) region is also important for the thermostability of thermolysin.

Site-directed mutations aimed at stabilizing thermolysin should involve the regions around residues 4, 19, 56–69 (59–72), 103 (106), and 182 (185).

Thermolysin can be stabilized by replacing residues by the corresponding residue in NP-ste. This obviously does not apply to residues 4, 56 (59), 58 (61), 63 (66) and 69 (72); it does apply to for example residues 19, 103 (106), and 182 (185) and to other, so far unidentified residues.

These conclusions make clear how thermolysin could be stabilized by site-directed mutations.

FIGURE LEGENDS

FIG. 1

Amino acid sequence of the mature extracellular neutral protease secreted by B. stearothemophilus CU-21 and nucleotide sequence of the corresponding part of the nprT gene encoding this protein (Takagi et al., 1985). The amino acid sequence denoted by 'NP-ste' in this figure belongs to the protein that is referred to in this invention as 'the neutral protease of B. stearothemophilus'. In the present invention this protein was obtained by expressing the nprT gene in B. subtilis. The sequence that was published for this protein contained an Asn at position 259 (Takagi et., 1985). Further sequence analysis showed that this was an error and that position 259 is a Thr as indicated in the figure (unpublished observations by the inventors). The numbers in the figure refer to the numbering of the amino acid sequence of the mature, secreted neutral protease.

FIG. 2

Amino acid sequence of the mature extracellular neutral protease secreted by B. thermoproteolyticus (Thermolysin; TLN) and nucleotide sequence of the corresponding part of the tin gene encoding this protein (Takagi et al., 1985). The amino acid sequence denoted by TLN in this figure differs at two positions (indicated by ***) from the sequence originally described for Thermolysin (see Titani et al., 1972): it has Asn at position 37 instead of Asp, and Gln at position 119 instead of Glu. It is most likely that the sequence presented in this figure (which was derived from a nucleotide sequence) is more accurate than the sequence originally published by Titani et al. (1972) (which was determined by direct sequencing of the protein). In this invention it is assumed that Thermolysin contains indeed Asn at position 37 and Gln at position 119. The numbers in the figure refer to the numbering of the amino acid sequence of the mature, secreted neutral protease.

FIGS. 3A and 3B

Alignment of the amino acid sequences of the mature extracellular neutral proteases secreted by B. thermoproteolyticus (thermolysin, TLN; Marquardt et al., 1990; the corresponding part of the gene encoding this protease, tln, is indicated), and by B. stearothermophilus CU21 (NP-ste; Takagi et al., 1985; the corresponding part of the gene encoding this protease, nprT, is indicated).

The amino acid sequence denoted by 'NP-ste' in this figure belongs to the protein that is referred to in this invention as 'the neutral protease of B. stearothermophilus'. In the present invention this protein was obtained by expressing the nprT gene in B. subtilis. The sequence that was published for this protein contained an Asn at position 259 (Takagi et al., 1985). Further sequence analysis showed that this was an error and that position 259 is a Thr as indicated in the figure (unpublished observations by the inventors).

The amino acid sequence denoted by TLN in this figure differs at two positions (indicated by ***) from the sequence originally described for thermolysin (see Titani et al., 1972): it has Asn at position 37 instead of Asp, and Gln at position 119 instead of Glu. It is most likely that the sequence presented in this figure (which was derived from a nucleotide sequence) is more accurate than the sequence originally published by Titani et al. (1972) (which was determined by direct sequencing of the protein). In this invention it is assumed that thermolysin contains indeed Asn at position 37 and Gln at position 119. Thermolysin was obtained form Boehringer Mannheim.

The numbers in the figure refer to the numbering of the amino acid sequences of the mature, secreted neutral proteases. Residues in NP-ste that differ from the corresponding residue in thermolysin are printed in bold letter type. Counting the three amino acid insertion in NP-ste as one difference, the total number of positions differing between NP-ste and TLN is 44.

FIG. 4

Typical thermostability (T50) curves for the wild-type B. stearothermophilus neutral protease and two variants of this enzyme in which various amino acid residues were changed. The figure shows T50 curves for wild-type NP-ste (+), thermolysin (Δ), and a five-fold (o; Thr4, Ala59, Ala61, Phe66 and Pro72) and a six-fold (+; Thr4, Ala59, Ala61, Phe66, Pro68 and Pro72) mutant of NP-ste. The thermostability assays were performed with enzymes that were purified from culture supernatants of B. subtilis DB117 strains harbouring plasmid pGE501 or a mutated variant thereof that carried respectively a wild-type or a variant of the gene encoding the B. stearothermophilus neutral protease. The picture shows the relative residual proteolytic activity in samples that were incubated for 30 minutes at various temperatures (pH=5.3).

FIG. 5

Stability of the wild-type B. stearothermophilus neutral protease (+), thermolysin (Δ) and the most stable neutral protease variant claimed here (o), in time, at 90° C. The picture shows the relative residual proteolytic activity in samples that were incubated at 90° C., at pH=5.3, for different periods of time.

LITERATURE

Alber, T. (1989). Mutational effects on protein stability. *Annu. Rev. Biochem.* 58, 765–798.

Aoki, T., Noguchi, N., Sasatsu, M. & Kono, M (1987). Complete nucleotide sequence of pTZ12, a chloramphenicol-resistance plasmid of *Bacillus subtilis*. *Gene* 51, 107–111.

Braxton, S., & Wells, J. A. (1992). Incorporation of a stabilizing $Ca^{2+}$-binding loop into subtilisin BPN'. *Biochem.* 31, 7796–7801.

Chothia, C. & Lesk, A. M. (1986). The relation between the divergence of sequence and structure in proteins. *EMBO J.* 5, 823–826.

Dahlquist, F. W., Long, J. W., & Bigbee, W. L. (1976). Role of calcium in thermal stability of thermolysin. *Biochem.* 15, 1103–1111.

Eijsink, V. G. H., Vriend, G., Van den Burg, B., Venema, G. & Stulp, B. K. (1990). Contribution of the C-terminal amino acid to the stability of *Bacillus subtilis* neutral protease. *Protein Engineering* 4, 99–104.

Eijsink, V. G. H. (1991). Engineering the thermostability of Bacillus neutral proteases. Academic thesis, Groningen State University.

Eijsink, V. G. H., Van der Zee, J. R., Van den Burg, B., Vriend, G. & Venema, G. (1991a). Improving the thermostability of the neutral protease of *Bacillus stearothermophilus* by replacing a buried asparagine by leucine. *FEBS letters* 282, 13–16.

Eijsink, V. G. H., Van den Burg, B. & Venema, G. (1991b). High performance affinity chromatography of Bacillus neutral proteases. *Biotechnol. Appl. Biochem.* 14, 275–283

Eijsink, V. G. H., Van den Burg, B., Vriend, G., Berendsen, H. J. C., & Venema, G. (1991c). Thermostability of *Bacillus subtilis* neutral protease. *Biochem. International* 24, 517–525.

Eijsink, V. G. H., Vriend, G., Van der Zee, J. R., Van den Burg, B. & Venema, G. (1992a). Increasing the thermostability of the neutral protease of *Bacillus stearothermophilus* by improvement of internal hydrogen bonding. *Biochem. J.* 285, 625–628.

Eijsink, V. G. H., Dijkstra, B. W., Vriend, G., van der Zee, J. R., Veltman, O. R., van der Vinne, B., van den Burg, B., Kempe, S. & Venema, G. (1992b). The effect of cavity-filling mutations on the thermostability of *B. stearothermophilus* neutral protease *Protein Engng.* 5,421–426.

Eijsink, V. G. H., Vriend, G., Van der Vinne, B., Hazes, B., Van den Burg, B., & Venema, G. (1992c). Effects of changing the interaction between subdomains on the thermostability of Bacillus neutral proteases. *Proteins Struct. Funct. Genet.* 14, 224–236.

Eijsink, V. G. H., Vriend, G., Hardy, F., Veltman, O. R., van der Vinne, B., van den Burg, B., Dijkstra, B. W., van der Zee, J. R. & Venema, G. (1993). Structural determinants of the thermostability of thermolysin-like Bacillus neutral proteases. In: Stability and stabilization of enzymes (W. F. van den Tweel et all, eds.), Esevier Science Publishers, pp. 91–99.

Fersht, A. R. & Serrano, L. (1993). principles of protein stability derived from protein engineering experiments. *Curr. Opinion Struct. Biol.* 3, 75–83.

Fujii, M., Takagi, M., Imanaka, T., & Aiba, S. (1983). Molecular cloning of a thermostable neutral protease gene from *Bacillus stearothermophilus* in a vector plasmid and its expression in *Bacillus stearothermophilus* and *Bacillus subtilis*. *J. Bacteriol.* 154, 831–837.

Geisow, M. J. (1991). Stabilizing protein products: coming in from the cold. *Trends in Biotechnol.* 9, 149–150.

Gerhartz (ed.) (1990). Enzymes in industry. VCH Verlagsgesellschaft, Weinheim, Germany.

Hardy, F., Vriend, G., Van der Vinne, B., Venema, G., & Eijsink, V. G. H. (1993). Stabilization of *Bacillus stearothemophilus* neutral protease by introduction of prolines. *FEBS lett.* 317, 89–92.

Holmes, M. A., & Matthews, B. W. (1982). Structure of thermolysin refined at 1.6 Å resolution. *J. Mol. Biol.* 160, 623–639.

Imanaka, T., Shibazaki, M., & Takagi, M. (1986). A new way of enhancing the stability of proteases. *Nature* 324, 695–697.

Isowa, Y., Ohmori, M., Ichikawa, T., Mori, K., Nonaka, Y., Kihara, K., Qyama, K., Satoh, H. & Nishimura, S. (1979). The thermolysin-catalyzed condensation reactions of N-substituted aspartic and glutamic acids with phenylalanine alkyl esters. *Tetrahedron letters* 28, 2611–2612.

Kristjansson, J. K. (1989). Thermophilic organisms as sources of thermostable enzymes. *Trends in Biotechnol.* 7, 349–353.

Kubo, M. & Imanaka, T (1988). Cloning and nucleotide sequence of the highly thermostable neutral protease gene from *Bacillus stearothermophilus*. *J. Gen. Microbiol.* 134, 1883–1892.

Kubo, M., Mitsuda, Y., Takagi, M. & Imanaka, T. (1992). Alteration of specific activity and stability of thermostable neutral protease by site-directed mutagenesis. *Appl. Environm. Microbiol.* 58, 3779–3783.

Marquardt, R., Hilgenfeld, R. & Keller, R. (1990). Proteasegen aus *Bacillus thermoproteolyticus rokko*, Verfahren zu seiner Gewinnung und seine Verwendung. European patent EP 90 11 6858/0 418 625 A1.

Matthews, B. W. (1991). Mutational analysis of protein stability. *Curr. Opinion in Struct. Biol.* 1, 17–21.

Nosoh, Y. & Sekiguchi, T. (1990). Protein engineering for thermostability. *Trends in Biotechnol.* 8, 16–20.

Sambrook, J., Fritsch, E. F. & Maniatis, T. (1989). Molecular cloning: a laboratory manual, 2nd ed. Cold Spring Harbor Laboratory, Cold Spring Harbor, N.Y., USA.

Sander, C. & Schneider, R. (1991). Database of homology-derived protein structures and the structural meaning of sequence alignment. *Proteins* 9, 56–68.

Sanger, F., Nicklen, S. & Coulson, A. R. (1977). DNA sequencing with chain-terminating inhibitors. *Proc. Natl. Acad. Sci. USA*, 74, 5463–5467.

Sonnleitner, B. & Fiechter, A. (1983). Advantages of using thermophiles in biotechnological processes: expectations and reality. *Trends in Biotechnol.* 1, 74–80.

Stanssens, P., Opsomer, C., Mckeown, Y. M., Kramer, W., Zabeau, M. & Fritz, H.-J (1989). Efficient oligonucleotide directed construction of mutations in expression vectors by the gapped duplex DNA method using alternating selectable markers. *Nucl. Acids Res.* 17, 4441–4454.

Stark, W., Pauptit, R. A., Wilson, K. S., & Jansonius, J. N. (1992). The structure of neutral protease from Bacillus cereus at 0.2-nm resolution. *Eur. J. Biochem.* 207, 781–791.

Takagi, M., Imanaka, T., & Aiba, S. (1985). Nucleotide sequence and promoter region for the neutral protease gene from *Bacillus stearothermophilus*. *J. Bacteriol.* 163, 824–831.

Titani, K., Hermodson, M. A., Ericsson, L. H., Walsh, K. A., & Neurath, H. (1972). Amino acid sequence of thermolysin. *Nature* 238, 35–37.

Toma, S., Campagnoli, S., Margarit, I., Gianna, R., Grandi, G., Bolognesi, M., De Filippis, V., & Fontana, A. (1991). Grafting of a calcium-binding loop of thermolysin to *Bacillus subtilis* neutral protease. *Biochem.* 30, 97–106.

Van den Burg, B., Eijsink, V. G. H., Stulp, B. K., & Venema, G. (1989). One-step affinity purification of Bacillus neutral proteases using bacitracin-silica. *J. Biochem. Biophys. Meth.* 18, 209–220.

Van den Burg, B. (1991). Protein engineering of Bacillus neutral proteases: effects on autodigestion and stability. Academic thesis, Groningen State University.

Van den Burg, B., Enequist, H. G., Van der Haar, M. E., Eijsink, V. G. H., Stulp, B. K., & Venema, G. (1991). A highly thermostable neutral protease from *Bacillus caldolyticus*, cloning and expression of the gene in *Bacillus subtilis* and characterization of the gene product. *J. Bacteriol.* 173, 4107–4115.

Vriend, G., Berendsen, H. J. C., Van der Zee, J. R., Van den Burg, B., Venema, G. & Eijsink, V. G. H. (1991). Stabilization of the neutral protease of *Bacillus stearothermophilus* by removal of a buried water molecule. *Protein Engineering* 4, 941–945.

Vriend, G., & Eijsink, V. G. H. (1993). Prediction and analysis of structure, stability and unfolding of Bacillus neutral proteases. *J. Computer-Aided Mol. Design* 7, 367–396.

Yang, M., Ferrari, E. & Henner, D. J. (1984). Cloning of the neutral protease gene of *Bacillus subtilis* and the use of the clone to create an in vitro-derived deletion mutant. *J. Bacteriol.* 160, 15–21.

Zell, R. & Fritz, H.-J. (1987). DNA mismatch-repair in *Escherichia coli* counteracting the hydrolytic deamination of 5-methyl-cytosine residues. *EMBO J.* 6, 1809–1815.

---

What is claimed is:

1. A method for producing a neutral protease having higher thermostability than thermolysin comprising site directed mutagenesis of the DNA coding for the neutral protease of SEQ ID NO: 3 at the weak regions which correspond to residues 1–25, 59–72, 106, and 189 of SEQ ID NO: 3, wherein said site-directed mutagenesis provides replacement of three amino acid residues located at residues 59, 66, and 72 or 61, 66, and 72 of SEQ ID NO: 3 in the N-terminal domain of said protease by the corresponding residue in thermolysin.

2. A polypeptide having metallo-endopeptidase activity obtainable by a method according to claim 1.

* * * * *